United States Patent [19]

Stirling

[11] 4,242,262
[45] Dec. 30, 1980

[54] 9-NITROMETHYLDEOXYCLAVULANIC ACID DERIVATIVES PREPARATION AND COMPOSITIONS

[75] Inventor: Irene Stirling, Reigate, England

[73] Assignee: Beecham Group Limited, England

[21] Appl. No.: 962,329

[22] Filed: Nov. 20, 1978

[30] Foreign Application Priority Data

Nov. 29, 1977 [GB] United Kingdom .............. 49730/77

[51] Int. Cl.$^3$ .................... C07D 498/04; A61K 31/42
[52] U.S. Cl. ................................. 260/245.3; 424/246; 424/271; 424/272
[58] Field of Search ...................... 260/307 FA, 245.3; 424/272

[56] References Cited

PUBLICATIONS

Cherry et al., Chem. Abs. 89, 59891g.

Primary Examiner—Mark L. Berch
Attorney, Agent, or Firm—Jacobs & Jacobs

[57] ABSTRACT

The present invention provides the compound of the formula (II):

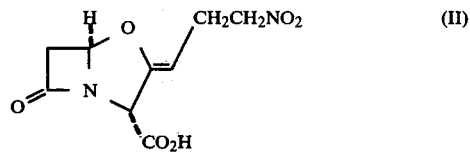

and salts and esters thereof.

6 Claims, No Drawings

9-NITROMETHYLDEOXYCLAVULANIC ACID DERIVATIVES PREPARATION AND COMPOSITIONS

Belgian Pat. No. 849308 discloses inter alia the compounds of the formula (I):

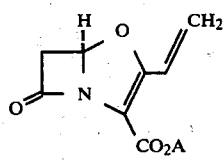
(I)

wherein A is a group such that $CO_2A$ is an ester group. It has now been found that such compounds may be converted to novel clavulanic acid derivatives which are able to enhance the effectiveness of penicillins and cephalosporins by virtue of their $\beta$-lactamase inhibitory properties and which have antibacterial activity.

Accordingly the present invention provides the compound of the formula (II):

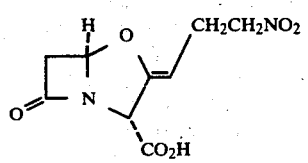
(II)

and salts and esters thereof.

Aptly the compound of the formula (II) is in the form of free acid.

Salts of the compound of the formula (II) are favoured. Pharmaceutically acceptable salts may be employed in medicaments whereas pharmaceutically non-acceptable salts may be used as intermediates in the preparation of the pharmaceutically acceptable salts or of esters.

More favourably the compound of the formula (II) is in the form of a salt such as an alkali metal or alkaline earth metal salt or salt with a nitrogenous base such as ammonia or an organic amine.

Suitable alkali metal salts of the compound of the formula (II) include the lithium, sodium and potassium salts. The lithium salt is envisaged primarily as an intermediate whereas the sodium and potassium salts may be used in pharmaceutical compositions or may be employed as intermediates.

Suitable alkaline earth metal salts of the compound of the formula (II) include the calcium and magnesium salts.

Suitable salts with nitrogenous bases include those with ammonia, alkylamines such as trimethylamine or triethylamine and salts with cyclic amines such as pyrrolidine or piperidine. Other favoured amine salts are those of primary alkylamines in which the amino group is attached to a trialkyl substituted carbon atom, for example the t-butyl amine salt is favoured.

Suitably the compounds of this invention are in the form of an ester such as of the formula (III):

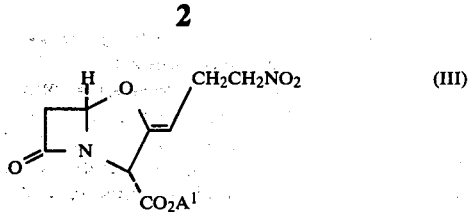
(III)

wherein the group $A^1$ is a group of the formula $A_1$ or $CHA_2A_3$ wherein $A_1$ is an alkyl group of up to 6 carbon atoms optionally substituted by an alkoxyl or acyloxyl group of 1–7 carbon atoms; $A_2$ is an alkenyl or alkynyl group of up to 5 carbon atoms or is a phenyl group optionally substituted by fluorine, chlorine, bromine, nitro or alkyl or alkoxyl of up to 4 carbon atoms; and $A_3$ is a hydrogen atom, an alkyl group of up to 4 carbon atoms or a phenyl group optionally substituted by fluorine, chlorine, bromine, nitro or alkyl or alkoxyl of up to 4 carbon atoms.

Certain favoured groups $A_1$ include the methyl, methoxymethyl, acetoxymethyl, acetoxyethyl, phthalidyl, ethoxycarbonyloxymethyl, $\alpha$-ethoxycarbonyloxyethyl and the like groups.

Certain favoured groups $A_2$ include the phenyl and 4-methoxyphenyl group. A further favoured group $A_2$ is the p-nitrobenzyl group. A particularly favoured moiety $A_3$ is the hydrogen atom.

Esters of the compound of the formula (II) are primarily envisaged as intermediates so that particularly suitable esters are hydrolysable or hydrogenolysable esters. Thus particularly apt esters include methyl, methoxymethyl, benzyl, nitrobenzyl, chlorobenzyl, methoxybenzyl, bromobenzyl and the like.

The present invention also provides pharmaceutical compositions which comprise a compound of this invention and a pharmaceutically acceptable carrier.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Injectable or infusable compositions of salts of a compound of the formula (II) are particularly suitable as high tissue levels of a compound of the formula (II) can occur after administration by injection or infusion. Thus, one preferred composition aspect of this invention comprises a salt of a compound of the formula (II) in sterile form.

Unit dose compositions comprising a compound of the formula (II) or a salt of ester thereof adapted for oral administration form a further preferred composition aspect of this invention.

The compound of the formula (II) or its salt or ester may be present in the composition as sole therapeutic agent or it may be present together with other therapeutic agents such as a $\beta$-lactam antibiotic. Suitable $\beta$-lactam antibiotics for inclusion in the compositions of this invention include benzylpenicillin, phenoxymethylpenicillin, carbenicillin, azidocillin, propicillin, ampicillin, amoxycillin, epicillin, ticarcillin, cyclacillin, cefatriazine, pirbenicillin, α-sulphonyloxybenzylpenicillin, cephaloridine, cephalothin, cefazolin, cephalexin, cephacetrile, cephamandole nafate, cephapirin, cephradine, 4-hydroxy-cephalexin, cefaparole, cephaloglycine and other well known penicillins and cephalosporins or pro-drugs therefor such as hetacillin, metampicillin, 4-acetoxyampicillin, the acetoxymethyl, ethoxycarbonyloxymethyl, pivaloyloxymethyl or phthalidyl esters of benzylpenicillin or ampicillin or the phenyl or indanyl α-esters of carbenicillin or ticarcillin or the like. Such compounds are frequently used in the form of a salt or hydrate.

Naturally if the penicillin or cephalosporin present in the composition is not suitable for oral administration then the composition will be adapted for parenteral administration.

When present together with a cephalosporin or penicillin, the ratio of a compound of the formula (II) or its salt or ester present to the other antibacterial agent may vary over a wide range of ratios, for example 3:1 to 1:10 and advantageously may be from 1:1 to 1:8, for example, 1:2, 1:3, 1:4, 1:5 or 1:6.

The total quantity of compound of the formula (II) in any unit dosage form will normally be between 25 and 1000 mg and will usually be between 50 and 500 mg, for example about 62.5, 100, 125, 150, 200 or 250 mg.

Compositions of this invention may be used for the treatment of infections of inter alia, the respiratory tract, the urinary tract and soft tissues and mastitis in cattle.

Normally between 50 and 1000 mg of the compounds of the invention will be administrated each day of treatment but more usually between 100 and 750 mg of the compounds of the invention will be administered per day, for example as 1-6 doses, more usually 2-4 doses.

The penicillin or cephalosporin in synergistic compositions of this invention will normally be present up to or at approximately the amount at which it is conventionally used.

Particularly favoured compositions of this invention will contain from 150-1000 mg of amoxycillin, ampicillin or a pro-drug therefor and from 25-500 mg of a compound of the formula (II) or salt or ester thereof and more suitably from 200-750 mg of amoxycillin or a salt thereof and from 50-250 mg of a salt of the compound of the formula (II).

Certain preferred compositions of this invention will contain amoxycillin trihydrate or a pharmaceutically acceptable salt of amoxycillin such as sodium amoxycillin.

The materials present in such compositions may be hydrated if required for example ampicillin trihydrate or amoxycillin trihydrate may be employed. The weights of the antibiotics in such compositions are expressed on the basis of antibiotic theoretically available from the composition and not on the basis of the weight of pro-drug.

Highly favoured compositions of this invention are those containing the compound of the formula (II) especially when of high purity and in crystalline form.

Penicillins suitable for inclusion in orally administrable compositions of this invention together with the compound of the formula (II) include benzylpenicillin, phenoxymethylpenicillin, propicillin, amoxycillin, ampicillin, epicillin, cyclacillin, and other orally active penicillins and their salts and in-vivo hydrolysable esters and aldehyde and ketone adducts of those penicillins containing a 6-α-aminoacylamino side chain and their salts. Suitable penicillin in-vivo hydrolysable esters include the acetoxymethyl, pivaloyloxymethyl, α-ethoxycarbonyloxyethyl and phthalidyl esters of ampicillin or amoxycillin or the phenyl, tolyl and indanyl α-esters of carbenicillin and ticarcillin and salts thereof.

Suitable aldehyde and ketone adducts of penicillins containing a 6-α-aminoacylamino side chain include the formaldehyde and acetone adducts metampicillin and hetacillin and their salts. Suitable penicillins for inclusion in injectably or infusably administrable compositions together with the compound of the formula (II) include the acceptable salts of benzylpenicillin, phenoxymethylpenicillin, carbenicillin, propicillin, cyclacillin and other known penicillins such as pirbencillin, azlocillin, mezlocillin or the like.

Cephalosporins suitable for inclusion in orally administrable compositions of this invention together with the compound of the formula (II) include cephalexin, cephradine, cephaloglycine, cephaparole and their salts and other known cephalosporins and their salts and in-vivo hydrolysable esters and aldehyde and ketone adducts of those cephalosporins containing a 7-α-aminoacylamino side chain and their salts. Suitable cephalosporins for inclusion in the injectable or infusable compositions of this invention together with the compound of the formula (II) include the salts of cephaloridine, cephalothin, cefazolin, cephalexin, cephacetrile, cephamandole, cephapirin, cephradine, cephaloglycine, cephatriazine and other known cephalosporins.

The present invention provides a process for the preparation of the compound of the formula (II) or a salt or ester thereof which process comprises the reaction of a compound of the formula (I) with the carbanion of of nitromethane and thereafter converting the initially produced ester of the compound of the formula (II) into the compound of the formula (II) or a salt thereof and thereafter if desired converting the thus produced compound of the formula (II) or salt thereof into an alternative ester of the compound of the formula (II).

The carbanion of nitromethane may be generated by the reaction of nitromethane with a strong base such as an alkali metal hydride (such as sodium hydride), a lithium amide or alkyl (such as lithium di-isopropylamide or butyl lithium) an alkoxide (such as potassium tert-butoxide) or the like. The carbanion is generated before introduction to the diene. Care should be takem that no free nucleophilic base is present when the carbanion and diene are mixed. This is conveniently effected by using an excess of nitromethane.

The condensation reaction is performed in an organic solvent such as dimethylformamide, tetrahydrfuran, dimethylsulphoxide or the like. Frequently free nitromethane may be present in the reaction mixture in solvent quantities.

In general the reaction is initially carried out at a non-elevated temperature, for example −20° to +40° C., more usually about −10° to +5° C., for example at about 0° C. After stirring at such temperatures for some time (for example 15 to 100 minutes) the reaction mixture may be allowed to warm to ambient temperature.

The desired ester may be obtained from the reaction mixture by such conventional methods as washing (after dilution with a water immiscible solvent if original solvent is water miscible), drying and evaporation. Purification if required may be effected chromatographically, for example on silica gel using cyclohexane/ethyl acetate followed by evaporation of the relevant fractions (identified by thin layer chromatography using permanganate spray).

The present invention also provides a process for the preparation of the compound of the formula (II) or a salt thereof which comprises the de-esterification of an ester of the compound of the formula (II).

De-esterification of esters of the compound of the formula (II) may be effected by hydrogenation or hydrolysis.

The acid and salt formation may be effected as described in British patent Specification Nos. 1508977 and 1508978 and Belgian Pat. Nos. 827926 and 847045.

A particularly suitable method of hydrogenolysis employs benzyl esters or substituted benzyl esters such as p-bromobenzyl, p-methoxybenzyl or p-nitrobenzyl esters.

Esterification of the compound of the formula (II) or its salts may be effected by the processes of the aforementioned patents and patent applications.

The following Examples illustrate the invention:

EXAMPLE 1

Benzyl 9-nitromethyldeoxyclavulanate

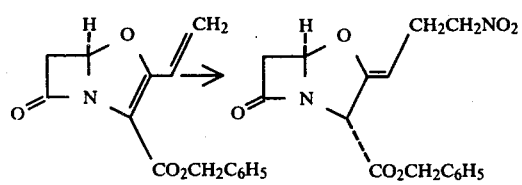

Nitromethane (1.8 g; 0.03 mol) was treated with sodium hydride (0.144 g; 50% dispersion in oil, 0.003 mol) at 0° C. Dry dimethylformamide (3 ml) was added followed by a solution of benzyl clavudiene (0.81 g; 0.003 mol) in nitromethane (1.8 g; 0.03 mol). The resulting yellow solution was stirred at 0° C. for 1 hour and at room temperature for 1 hour. Ethyl acetate was added to the solution which was washed with water, brine, dried and evaporated. The dark yellow oily residue was subjected to column chromatography on silica gel. Elution with cyclohexane/ethyl acetate (2:1) gave the desired product (0.35 g, 35.5% yield) as a colourless oil; (Found C, 58.08; H, 4.84; N, 8.56%; $C_{16}H_{16}N_2O_6$ requires C, 57.83; H, 4.85; N, 8.43%); $\nu$max (CHCl$_3$) 1810, 1755, 1704 cm$^{-1}$; $\delta$ (CDCl$_3$) 2.70 (2H, q, J 7 Hz, $=$CHC$\underline{H}_2$CH$_2$), 2.98 (1H, d, J 17 Hz, 6$\beta$—C$\underline{H}$), 3.42 (1H, dd, J 17 and 3 Hz, 6$\alpha$—C$\underline{H}$), 4.25 (2H, t, J 7 Hz, $=$CH.CH$_2$C$\underline{H}_2$), 4.50 (1H, dt, J 7 and 1.5 Hz, $=$C$\underline{H}$CH$_2$), 4.98 (1H, d, J 1.5 Hz, 3—C$\underline{H}$), 5.12 (2H, s, C$\underline{H}_2$C$_6$H$_5$), 5.62 (1H, d, J 3 Hz, 5—C$\underline{H}$), 7.28 (5H, s, Ar—$\underline{H}$).

| | MIC ($\mu$g/ml) | | | |
|---|---|---|---|---|
| | Staph. Russell | Kleb. E 70 | Proteus C 889 | E. coli JT 39 |
| Ampicillin alone | 125 | > 500 | > 500 | > 500 |
| Ampicillin + compound of Example 1 1.0$\mu$/ml | 3.1 | 50 | 250 | 125 |
| Ampicillin + compound of Example 1 5.0$\mu$/ml | 0.4 | 3.1 | 31 | 8.0 |
| Ampicillin + compound of Example 1 20 $\mu$/ml | — | 1.5 | 4 | 4.0 |

EXAMPLE 2

Lithium 9-nitromethyldeoxyclavulanate

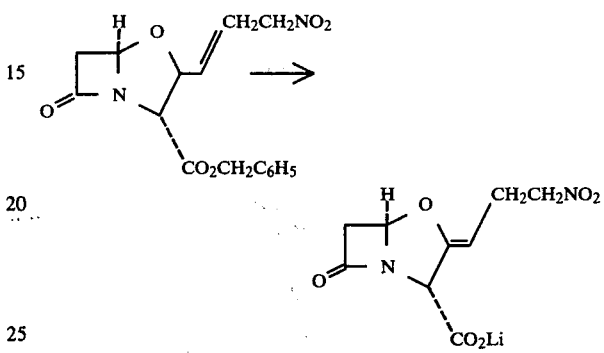

Benzyl 9-nitromethyldeoxyclavulanate (67 mg) was dissolved in dry redistilled tetrahydrofuran (10 ml) and hydrogenolysed at N.T.P. over 10% palladised charcoal (20 mg) for 30 minutes. The suspension was filtered and the filtrate, containing the free acid, was titrated with 1 M lithium hydroxide solution to ca. pH 7.5 (pH meter). Solvent was removed in vacuo and the solid residue triturated with acetone/ether and filtered to give the product as a white powder (30 mg, 60% yield); $\nu$max (KBr) 1775, 1695, 1620 cm$^{-1}$; $\delta$(D$_2$O) [acetonitrile as internal standard ($\delta$2.00)], 2.71 (2H, bq, J 6 Hz, $=$CH.C$\underline{H}_2$), 2.99 (1H, d, J 17 Hz, 6$\beta$-C$\underline{H}$), 3.49 (1H, dd, J 17 and 3 Hz, 6$\alpha$-C$\underline{H}$), 4.51 (2H, t, J 7 Hz, $=$CH.CH$_2$C$\underline{H}_2$), 4.83 (1H, s 3-C$\underline{H}$), 5.62 (1H, d, J 3 Hz, 5-C$\underline{H}$), methine proton at C-8 obscured by H$_2$O peak at $\delta$4.6).

| | Staph. Russell | Kleb. E 70 | Proteus C 889 | E. Coli JT 39 |
|---|---|---|---|---|
| Ampicillin alone | 125 | 22 500 | > 500 | > 500 |
| Ampicillin + compound of Example 2 1$\mu$/ml | 0.4 | 12.5 | 31 | 8 |
| Ampicillin + compound of Example 2 5$\mu$/ml | <0.01 | 1.5 | 2 | 4.0 |

EXAMPLE 3 p-Nitrobenzyl 9-nitromethyldeoxyclavulanate

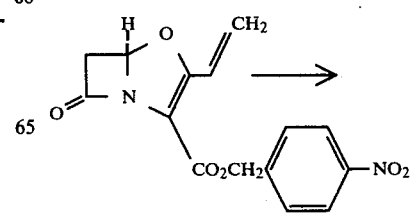

-continued

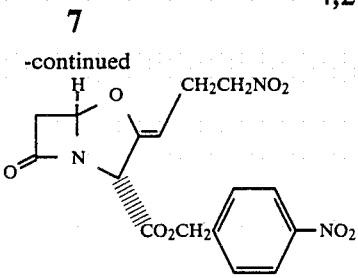

Nitromethane (1.87 g; 31 m.mol) was treated with sodium hydride (0.144 g of a 50% dispersion in oil; 3 m.mol) at 0°. Dimethylformamide (2 ml) was added to obtain a fine suspension; to this stirred suspension was added p-nitrobenzylclavudiene (0.97 g; 3.1 m.mol) in nitromethane (1.87 g) and the reaction mixture stirred at 0° for 30 mins. and at room temperature for two hours. The solution was poured into ethyl acetate, washed with water, brine, dried and evaporated. Column chromatography on silica gel using ethyl acetate/cyclohexane as the eulting solvent afforded the title compound which crystallised from ethanol/ether as colourless needles in 23% yield m.p. $\nu_{max}$ (Nujol)1795, 1750, 1697, 1695(sh) cm$^{-1}$. (Found C, 51.07; H, ;b 4.04; N, 11.00%; $C_{16}H_{15}N_3O_8$ requires C, 50.93; H, 4.00; N, 11.14%).

EXAMPLE 4 p-Nitrobenzyl 9-nitromethyldeoxyclavulanate

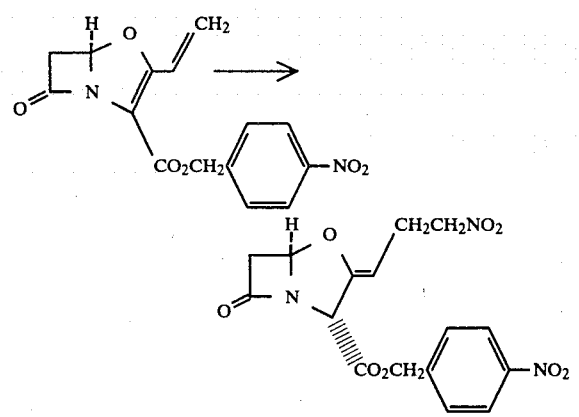

Nitromethane (3.74 g; 62 m.mol) was added to a three-necked oven-dried flask which was charged with nitrogen. Butyl lithium (1.89 ml of 1.62 M solution in hexane; 3.1 m.mol) was added via a syringe through a septum, at 0°. After ten minutes a solution of p-nitrobenzyl clavudiene (0.97 g; 3.1 m.mol) in nitromethane (1.87 g) and dimethylformamide (2 ml) was added. The temperature was allowed to rise to room temperature and the mixture stirred for two hours. The solution was poured into ethyl acetate and the organic phase washed with water, brine, dried and evaporated. The residue was chromatographed on silica gel and the product eluted with ethyl acetate/cyclohexane, 1:1. The title compound was obtained in 20% yield. $\nu_{max}$ (CHCl$_3$) 1802, 1750, 1695 cm$^{-1}$; δ2.77(2H, q, J 7 Hz,=CH.C$\underline{H}_2$CH$_2$), 3.04(1H, d, J 17 Hz, 6β-C$\underline{H}$), 3.51(1H, dd, J 17 and 3 Hz, 6α-C$\underline{H}$), 4.38 (2H, t, J 7 Hz, =CH.CH$_2$C$\underline{H}_2$NO$_2$), 4.62(1H, dt, J 7 and 1.5 Hz, 8—C$\underline{H}$), 5.08(1H, bs, 3—C$\underline{H}$), 5.26(2H, s, C$\underline{H}_2$C$_6$H$_4$—p—NO$_2$), 5.68(1H, d, J 3 Hz, 5—C$\underline{H}$), 7.49, 8.22(4H, ABq, AR-$\underline{H}$). M$^+$—NO 347.0894; $C_{16}H_{15}N_2O_7$ requires: 347.0878.

EXAMPLE 5

Methoxymethyl 9-nitromethyldeoxyclavulanate

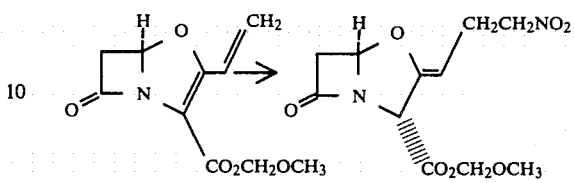

Sodium hydride (0.48 g of 50% dispersion in oil; 0.01 mol) was added to nitromethane (12.2 g; 0.2 mol) at 0°. After 10 mins. a solution of methoxymethyl clavudiene (2.25 g; 0.01 mol) in nitromethane (12.2 g) was added to the stirred suspension. The reaction mixture was stirred at room temperature for 4 hours and at 0° overnight after which t.l.c. showed almost complete disappearance of the diene. The solution was poured into ethyl acetate, washed with water, brine, dried and evaporated. The residue was subjected to column chromatography on silica gel using ethyl acetate/cyclohexane, 1:1 as the eluting solvent; the product was obtained as a colourless gum in 10% yield.

$\nu_{max}$ (CHCl$_3$) 1806, 1740(b), 1705 cm$^{-1}$; δ(CDCl$_3$) 2.77(2H, q, J 7 Hz, =CH.C$\underline{H}_2$CH$_2$), 3.04(1H, d, J 17 Hz, 6β-C$\underline{H}$), 3.5(1H, dd, J 17 and 3 Hz, 6α—C$\underline{H}$), 3.45(3H, s, CH$_2$OC$\underline{H}_3$), 4.39(2H, t, J 7 Hz, =CH.CH$_2$C$\underline{H}_2$NO$_2$), 4.66(1H, dt, J 7 and 1.5 Hz, 8—C$\underline{H}$), 5.04(1H, bs, 3—C$\underline{H}$), 5.23, 5.33(2H, ABq, J 6 Hz, C$\underline{H}_2$OCH$_3$), 5.68(1H, d, J 3 Hz, 5—C$\underline{H}$).

EXAMPLE 6

Benzyl 9-nitromethyldeoxyclavulanate

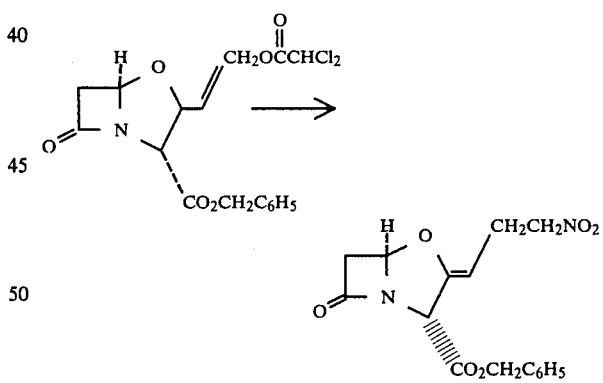

Nitromethane (9.1 g; 0.15 mol) was cooled to 0° and sodium hydride (1.44 g of 50% dispersion in oil; 0.03 mol) and dimethylformamide (2 ml) added. A solution of dichloroacetyl clavulanate (6 g; 0.015 mol) in nitromethane (9.1 g; 0.15 mol) was added to the cooled fine suspension and the reaction mixture was stirred at 0° for 30 mins. and at room temperature for 2 hours. The solution was poured into water and ethyl acetate and the organic phase was washed with water, brine, dried and evaporated to a yellow oil. The crude product was chromatographed on silica gel and the title compound was eluted with ethyl acetate/cyclohexane, 1:1 and isolated as a colourless oil in 40% yield. $\nu_{max}$ (CHCl$_3$) 1810, 1752, 1702 cm$^{-1}$.

EXAMPLE 7

Sodium 9-nitromethyldeoxyclavulanic acid

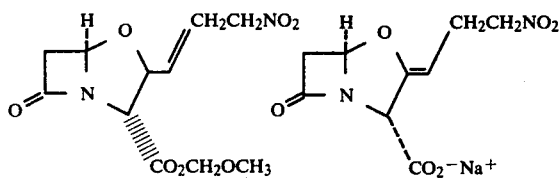

Methoxymethyl 9-nitromethyldeoxyclavulanate (100 mg) was dissolved in tetrahydrofuran/water, 1:3, and titrated with 1 M sodium hydroxide solution at pH 9.5 on a Metrohm pH-Stat. After uptake of the base had ceased, the solvent was removed in vacuo and the residue triturated with acetone/ether to give the required sodium salt as an off-white solid in 71% yield. $\nu_{max}$ (Nujol) 1785, 1695, 1620 cm$^{-1}$.

I claim:

1. A compound selected from the group consisting of 9-nitromethyldeoxyclavulanic acid of the formula:

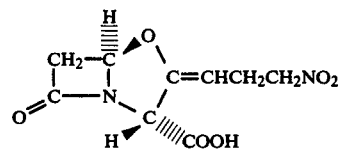

and the pharmaceutically acceptable salts thereof.

2. The compound according to claim 1 which is 9-nitromethyldeoxyclavulanic acid.

3. The compound according to claim 1 which is a pharmaceutically acceptable salt of 9-nitromethyldeoxyclavulanic acid.

4. The compound according to claim 3 which is the sodium or potassium salt.

5. An ester of 9-nitromethyldeoxyclavulanic acid of the formula:

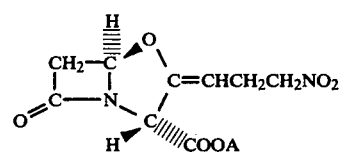

wherein A is alykl of 1 to 6 carbon atoms, methoxymethyl, acetoxymethyl, acetoxyethyl, phthalidyl, ethoxycarbonyloxymethyl, α-ethoxycarbonyloxyethyl, benzyl, nitrobenzyl, chlorobenzyl, methoxybenzyl or bromobenzyl.

6. An ester according to claim 5 in which A is selected from the group of methyl, methoxymethyl, benzyl, nitrobenzyl, chlorobenzyl, methoxybenzyl and bromobenzyl.

* * * * *